(12) United States Patent
He et al.

(10) Patent No.: US 11,891,355 B2
(45) Date of Patent: Feb. 6, 2024

(54) METHOD FOR PREPARING TAURINE AND METHOD FOR RECOVERING MOTHER LIQUOR THEREOF

(71) Applicants: ZHEJIANG NHU COMPANY LTD., Shaoxing (CN); ZHEJIANG NHU PHARMACEUTICAL CO., LTD., Shaoxing (CN); SHANGYU NHU BIO-CHEM CO., LTD., Shaoxing (CN)

(72) Inventors: Xiaoxiang He, Shaoxing (CN); Junhua Peng, Shaoxing (CN); Xianghua Yao, Shaoxing (CN); Songhua Xu, Shaoxing (CN); Lihuan Cheng, Shaoxing (CN); Yinbing Wang, Shaoxing (CN); Yinjiang Song, Shaoxing (CN); Lei Wang, Shaoxing (CN)

(73) Assignees: ZHEJIANG NHU COMPANY LTD., Shaoxing (CN); ZHEJIANG NHU PHARMACEUTICAL CO., LTD., Shaoxing (CN); SHANGYU NHU BIO-CHEM CO., LTD., Shaoxing (CN)

( * ) Notice: Subject to any disclaimer, the term of this patent is extended or adjusted under 35 U.S.C. 154(b) by 79 days.

(21) Appl. No.: 17/618,887

(22) PCT Filed: Nov. 17, 2020

(86) PCT No.: PCT/CN2020/129421
§ 371 (c)(1),
(2) Date: Dec. 14, 2021

(87) PCT Pub. No.: WO2021/120957
PCT Pub. Date: Jun. 24, 2021

(65) Prior Publication Data
US 2022/0371992 A1    Nov. 24, 2022

(30) Foreign Application Priority Data
Dec. 18, 2019 (CN) .......................... 201911312305.5

(51) Int. Cl.
C07C 303/44 (2006.01)
C07C 303/22 (2006.01)
C07C 303/32 (2006.01)

(52) U.S. Cl.
CPC .......... C07C 303/44 (2013.01); C07C 303/22 (2013.01); C07C 303/32 (2013.01)

(58) Field of Classification Search
None
See application file for complete search history.

(56) References Cited

U.S. PATENT DOCUMENTS

2021/0061758 A1*  3/2021  Chen ................... B01D 15/363

FOREIGN PATENT DOCUMENTS

| CN | 1807407 A | 7/2006 |
| CN | 101525306 A | 9/2009 |
| (Continued) | | |

OTHER PUBLICATIONS

Villamanan ("Excess Thermodynamic Functions for Ternary Systems. 11. Total-Pressure Data and GE for Ethylene Glycol/Acetone/Water and for Ethylene Glycol/Acetonitrile/Water at 50° C" J. Chem. Eng. Data. 1984 (29), p. 293-296) (Year: 1984).*

(Continued)

Primary Examiner — Amy C Bonaparte

(57) ABSTRACT

The present disclosure relates to a method for preparing taurine and a method for recovering a mother liquor thereof. The method for recovering the taurine mother liquor comprises: providing a taurine mother liquor, and mixing the taurine mother liquor and a treating agent to obtain a solid-containing suspension, wherein the treating agent is a water-soluble organic solvent or a mixture of the water- (Continued)

soluble organic solvent and water; filtering the suspension to obtain a first solid product and a first filtrate; and dissolving the first solid product with an ammonia source, and then filtering same to obtain a second solid product and a second filtrate.

11 Claims, 2 Drawing Sheets

(56) References Cited

FOREIGN PATENT DOCUMENTS

| | | |
|---|---|---|
| CN | 104829501 A | 8/2015 |
| CN | 108128829 A | 6/2018 |
| CN | 110483342 A | 11/2019 |

OTHER PUBLICATIONS

China Office Action of 202011254688.8, dated May 2022.
Wu, Di, "The Crystallization Process of Taurine", China Master's Theses Full-text Database, Engineering Technology, Feb. 28, 2018, pp. B024-B176, in particular p. 5, lines 12-14 and 19-32.
Lu, Jianping, "Studies on Preparation, Crystallizing and Drying of Taurine from Monoethanolamine", China Master's Theses Full-text Database, Engineering Technology, Mar. 31, 2016, pp. B016-B145, in particular p. 13, line 3 from the bottom to p. 14, line 5.
International Search Report of PCT/CN2020/129421 dated Jan. 20, 2021.

* cited by examiner

METHOD FOR PREPARING TAURINE AND METHOD FOR RECOVERING MOTHER LIQUOR THEREOF

CROSS-REFERENCE TO RELATED APPLICATION

This application is a National Stage application of International Application No. PCT/CN2020/129421 filed on Nov. 17, 2020, which claims all benefits accruing from China Patent Application No. 201911312305.5, filed on Dec. 18, 2019 in the China National Intellectual Property Administration, both of which are hereby incorporated by reference.

TECHNICAL FIELD

The present disclosure relates to the field of taurine, in particular, to a method for preparing taurine and a method for recovering the mother liquor thereof.

BACKGROUND

Taurine, also known as (3-amino ethanesulfonic acid, is a sulfur-containing non-protein amino acid, which is widely used in the fields of medicine, food additives, fluorescent whitening agent, organic synthesis and so on. The methods for preparing taurine include ethylene oxide method, ammonium taurate method, monoethanolamine method, ethanol method, and the like.

Among them, the ethylene oxide method is a main method for preparing taurine in conventional art. However, the method for preparing taurine by ethylene oxide method has the following problems: firstly, sodium isethionate is prone to produce by-products such as sodium ditaurate in a high temperature and high pressure reaction system (an equation of the ammonolysis reaction will be shown hereinafter), and by-products such as sodium ditaurate and residual sodium isethionate are highly soluble in water, and most of them remain in the mother liquor after an acidification and a separation processes; secondly, sodium taurate is generally neutralized with strong acids such as sulfuric acid, which is easy to produce a large amount of inorganic salt such as sodium sulfate, and it is difficult to separate the inorganic salts from taurine, besides, the inorganic salts remained in the mother liquor of taurine after the recovering treatment will derive into complex inorganic salts such as sodium sulfite, sodium sulfate, ammonium sulfite, ammonium sulfate and the like. Therefore, how to recover and treat effective ingredients such as sodium isethionate and sodium ditaurate, as well as impurity components such as inorganic salts and ethanediol in the taurine mother liquor has become a thorny issue.

The equation of the ammonolysis reactions are as below:

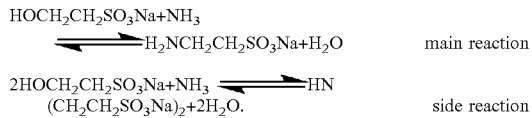

Currently, the method for recovering the mother liquor in industry is to reuse the crude mother liquor in an ammonification reaction, which can greatly increase the yield of the ammonification reaction. For example, Liu Fuming analyzed the final mother liquor of taurine in "Research on Ammonolysis Reaction Process of Taurine" published in Shandong Chemical Industry Vol. 44, page 26-30, 2015. The impurity components in the mother liquor are complex, mainly ingredients such as containing taurine, sodium isethionate, sodium sulfate, sodium imino diethanesulfonate, ethanediol, polyethylene glycol, and trace metal ions. In this paper, the final mother liquor is simply cooled or the ammonia content in the final mother liquor is increased, and then a certain amount of base is added to obtain a mixture having main ingredients of sodium isethionate, sodium taurate and sodium sulfate to participate in the ammonolysis reaction again. The higher the content of the mixture in the mother liquor, the higher the ammonolysis yield. However, the mother liquor content cannot be increased indefinitely in actual production, and the final mother liquor in the production can only meet a maximum reusing amount of 9.0% (v/v). In addition, the components in different batches of mother liquor are very different and the components are complex. Reusing the mother liquor in large-scale will have a great impact on the production stability of the ammonification reaction. In addition, since contents of inorganic salts in the mother liquor are higher than that of taurine, the process usually adopts concentrated and hot suction filtration to remove the salt. However, ammonium sulfite, ammonium sulfate, sodium sulfite and sodium sulfate are very easy to bond, and the separation of taurine and inorganic salts is difficult to achieve the desired effect. Inorganic salts will gradually accumulate during the circulations, and there is a risk of clogging the pipeline, and thus there is a greater safety hazard.

Chinese patents Nos. CN104447426A and CN106349123A respectively provide methods for separate taurine from a taurine mother liquor. In the two patents, a chromatographic column filled with adsorption-type amino acid resin and several sets of interconnected electrodialysis separation systems are respectively used to separate taurine and inorganic salts in the mother liquor containing a certain concentration of taurine and inorganic salts. However, the costs of the chromatographic column and the electrodialysis separation system used in the two patents are too high, which are not conducive to production. In addition, the components of the mother liquor processed in the two patents are too simple, containing only inorganic salts and taurine, and separation of other components in the mother liquor is not mentioned. They are not suitable for the treatment of taurine mother liquor with complex composition in actual production.

SUMMARY

On the basis of embodiments of the present disclosure, the present disclosure provides a method for recovering a taurine mother liquor, which includes:

A1, providing a taurine mother liquor, and mixing the taurine mother liquor and a treating agent to obtain a solid-containing suspension, wherein the treating agent is a water-soluble organic solvent or a mixture of the water-soluble organic solvent and water;

A2, filtering the suspension to obtain a first solid product and a first filtrate; and A3, dissolving the first solid product with an ammonia source to obtain a first mixture, and then filtering the first mixture to obtain a second solid product and a second filtrate.

In the method for recovering taurine in the present disclosure, the water-soluble organic solvent can precipitate effective ingredients (such as taurine, alkali metal taurate, alkali metal ditaurate, alkali metal tritaurate, alkali metal isethionate and the like) and inorganic salts (such as sulfates and the like) to form solid products. However, impurities such as ethanediol, polyethylene glycol, polyether and the like are soluble in the organic solvent. Thus, impurities such as ethanediol, polyethylene glycol, polyether and the like can be firstly separated from the taurine mother liquor by filtering. Then, the first solid product separated from the taurine mother liquor can be dissolved by the ammonia source. Since solubility of the inorganic salt containing in the first solid product is pretty low, the inorganic salt can precipitate out from the first mixture. However, effective ingredients (such as taurine, alkali metal taurate, alkali metal ditaurate, alkali metal tritaurate, alkali metal isethionate and the like) can solute in the ammonia source. Thus, inorganic salt impurities can be separated out again from the first mixture by filtering. Therefore, the second filtrate containing effective ingredients (such as taurine, alkali metal taurate, alkali metal ditaurate, alkali metal tritaurate, alkali metal isethionate and the like) can be recovered. The second filtrate can be directly circulated to a step of ammonolysis reaction of the alkali metal isethionate and the ammonia.

The method for recovering taurine mother liquor can remove most of main impurities such as ethanediol, inorganic salts, and the like, and have a good purification effect. Besides, recovery of effective ingredients, such as taurine, alkali metal taurate, alkali metal ditaurate, alkali metal tritaurate, alkali metal isethionate and the like, is high. The recovered effective ingredients can be directly circulated to the step of ammonolysis reaction, and improve yield of alkali metal taurate. In the method of the present disclosure, materials can be circulated in the reaction to reduce discharging of waste liquor. The method of the present disclosure is environmentally friendly and economical.

In some embodiments, a mass ratio of the taurine mother liquor and the organic solvent in step A1 is in a range of 1:1 to 1:20.

In some embodiments, the organic solvent in step A1 is at least one selected from alcohol, ketone and aldehyde.

In some embodiments, the alcohol includes at least one selected from alcohols containing one to six carbon atoms. The ketone includes at least one selected from acetone, butanone and methyl vinyl ketone. The aldehyde is at least one selected from aldehydes containing one to five carbon atoms.

In some embodiments, when the treating agent is the mixture of the water-soluble organic solvent and water, a mass fraction of water in the mixture is less than or equal to 50%.

In some embodiments, in step A1 a process of mixing the taurine mother liquor with the treating agent includes: adding the taurine mother liquor into the treating agent in batches, or, adding the treating agent into the taurine mother liquor in batches.

In some embodiments, before dissolving the first solid product in the ammonia source, step A3 further includes, drying the first solid product to make a mass fraction of the organic solvent in the first solid product less than or equal to 2%.

In some embodiments, the ammonia source in step A3 includes a saturated ammonium hydroxide.

In some embodiments, in step A3, a mass of the ammonia source is 4 times to 15 times of a mass of the dried first solid product.

In some embodiments, the first filtrate in step A2 includes ethanediol and the organic solvent, and step A2 further includes separating and recovering the organic solvent.

In some embodiments, the method further includes circulating the recovered organic solvent to step A1, and mixing the recovered organic solvent with the taurine mother liquor On the basis of embodiments of the present disclosure, the present disclosure further includes a method for preparing taurine, including, B1, providing an alkali metal isethionate, and mixing the alkali metal isethionate with ammonia to carry out an ammonolysis reaction to obtain an alkali metal taurate solution;

B2, subjecting the alkali metal taurate solution to neutral reaction to obtain a taurine solution;

B3, crystalizing the taurine solution to obtain taurine and the taurine mother liquor; and B4, recovering the taurine mother liquor via the method above to obtain the second filtrate.

In some embodiments, the method further incudes mixing the second filtrate obtained in step B4 with a base to obtain a second mixture, and circulating the second mixture to step B1 to carry out the ammonolysis reaction.

In some embodiments, a mass ratio of the base to the second filtrate is in a range of 0.5:100 to 5:100, and the base is at least one selected from NaOH, KOH, $Na_2CO_3$ and $NaHCO_3$.

In the method for preparing taurine in the present disclosure, recovery of effective ingredients such as taurine, alkali metal taurate, alkali metal ditaurate, alkali metal tritaurate, alkali metal isethionate, and the like in the taurine mother liquor is high, and removal rate of impurities such as inorganic salt, ethanediol, and the like is high. Thus, the recovered effective ingredients can be better circulated to the ammonolysis reaction. Therefore, materials can be circulated in the reaction to reduce discharging of waste liquor. The method in the present disclosure is environmentally friendly and economical, and can prevent inorganic salts from accumulating in the circulating process, thereby reducing potential safety hazards.

BRIEF DESCRIPTION OF THE DRAWINGS

In order to better describe and explain the embodiments and/or examples of those inventions disclosed herein, one or more drawings may be referred to. The additional details or examples used to describe the drawings should not be considered as limiting the scope of any of the disclosed inventions, the currently described embodiments and/or examples, and the best mode of these inventions currently understood.

DETAILED DESCRIPTION

A method for preparing taurine and a method for recovering a taurine mother liquor provided in the present disclosure will be further illustrated hereinafter.

Figure 1:
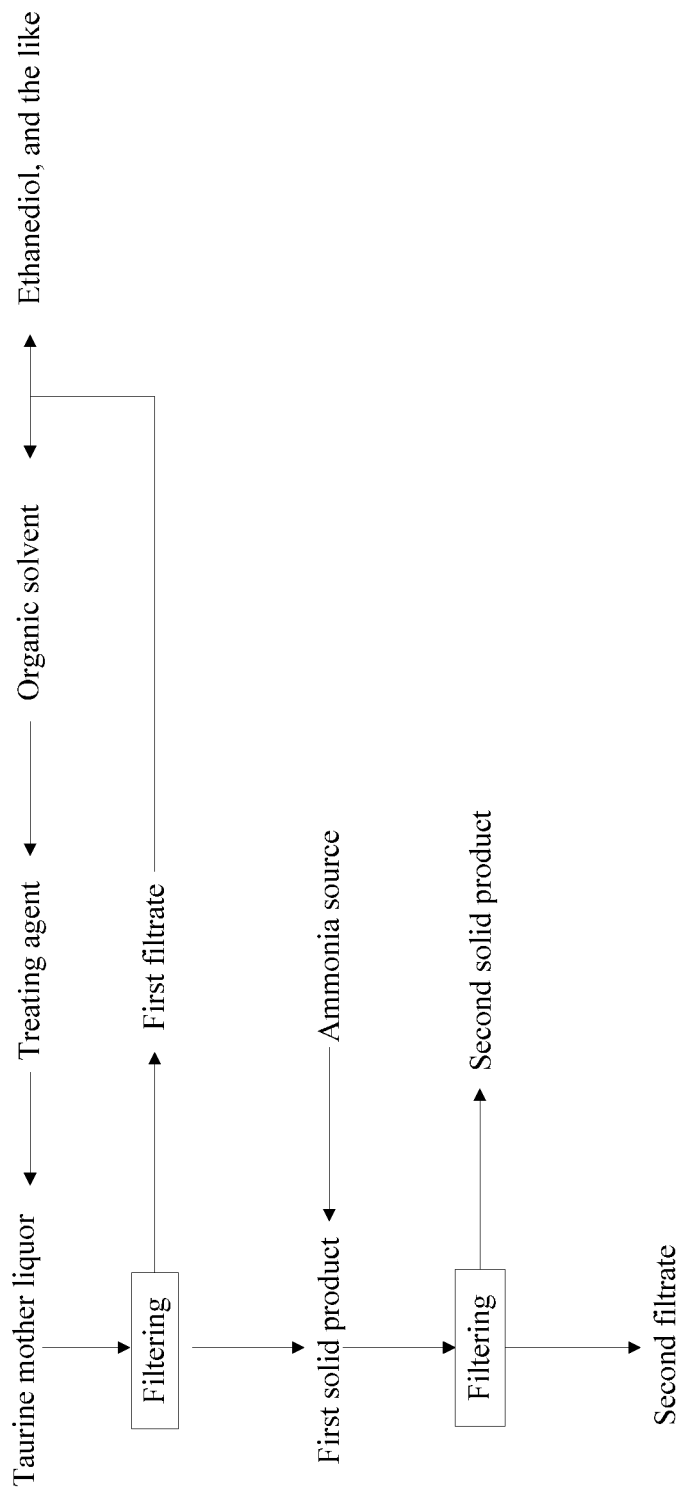
FIG. 1 is a flowchart of a method for recovering taurine mother liquor in the present disclosure.

FIG. 1 is a flowchart of a method for recovering taurine mother liquor in the present disclosure. The method includes:

A1, providing a taurine mother liquor, and mixing the taurine mother liquor and a treating agent to obtain a solid-containing suspension, wherein the treating agent is a water-soluble organic solvent or a mixture of the water-soluble organic solvent and water;

A2, filtering the suspension to obtain a first solid product and a first filtrate; and A3, dissolving the first solid product with an ammonia source to obtain a first mixture, and then filtering the first mixture to obtain a second solid product and a second filtrate.

In step A1, the taurine mother liquor can be a crystallization mother liquor for preparing crude taurine. In some embodiments, the crystallization mother liquor can be a taurine mother liquor which had been subjected to crystallization for over two times, to reduce a mass fraction of taurine in the mother liquor.

In some embodiments, before mixing the taurine mother liquor with the treating agent, the method can further include decoloring the taurine mother liquor, including decoloring by activated carbon adsorption or aluminum oxide.

Effective ingredients, such as taurine, alkali metal taurate, alkali metal ditaurate, alkali metal tritaurate, alkali metal isethionate and the like and inorganic salt impurities such as sulfate and the like, in the taurine mother liquor have a low solubility in the organic solvent. However, impurities, such as ethanediol, polyethylene glycol, polyether and the like, have a high solubility in the organic solvent. Therefore, after mixing the taurine mother liquor with the organic solvent, the effective ingredients and the inorganic salts can be precipitated out, and firstly separated from impurities that are soluble in the organic solvent such as ethanediol, polyethylene glycol, polyether, and the like.

In order to facilitate precipitation of the effective ingredients and the inorganic salts, the solubility of the organic solvent in water should be higher than that of the effective ingredients and the inorganic salts. In some embodiments, the organic solvent can be at least one selected from alcohol, ketone and aldehyde.

Considering that lower monohydric alcohols can be easier dried, in some embodiments the alcohol can include monohydric alcohol containing one to six carbons, including at least one selected from methanol, ethanol, n-propanol, isopropanol, allyl alcohol, n-butanol, isobutanol, 2-butanol, butenol, n-pentanol, isoamyl alcohol, n-hexanol, cyclopentanol, 2-methyl-2-butanol, and 3-methyl-2-butanol. In some embodiments, the alcohol can include at least one selected from methanol and ethanol. In the same way, the ketone can be a lower ketone selected from at least one from acetone, butanone and methyl vinyl ketone. The aldehyde can be least one selected from aldehydes containing one to five carbon atoms, including at least one selected from formaldehyde, acetaldehyde, propionaldehyde, glyoxal, malondialdehyde, butanedial, glutaraldehyde, acrolein and furfural.

When the treating agent is the mixture of the water-soluble organic solvent and water, a mass fraction of water in the mixture can be less than or equal to 50%. In some embodiments, the mass fraction of water in the mixture can be less than or equal to 10%. This can avoid influence of excess water on precipitation of effective ingredients such as taurine, alkali metal taurate, alkali metal ditaurate, alkali metal tritaurate, alkali metal isethionate and the like.

In order to facilitate precipitation of the effective ingredients and the inorganic salts, a mass ratio of the taurine mother liquor and the organic solvent can be in a range of 1:1 to 1:20. In some embodiments, the mass ratio of the taurine mother liquor and the organic solvent can be in a range of 1:3 to 1:10.

Specifically, a process of mixing the taurine mother liquor with the treating agent can include: adding the taurine mother liquor into the treating agent in batches, or, adding the treating agent into the taurine mother liquor in batches.

In some embodiments, the means of adding in batches can be dropwise adding while stirring, so that the taurine mother liquor can sufficiently mix with the organic solvent, thereby facilitating precipitation of the effective ingredients and the inorganic salts.

After fully precipitating the effective ingredients and the inorganic salts, in step A2, the suspension can be filtered, so as to obtain a first solid product containing the effective ingredients and the inorganic salts and a first filtrate containing ethanediol, polyethylene glycol and polyether. Therefore, impurities, such as ethanediol, polyethylene glycol, polyether and the like, can be separated out from the effective ingredients. The process is simple to operate.

In some embodiments, the first filtrate can be purified by methods such as distillation, rectification, permeable membrane treatment or column chromatography, so as to separate and recover the organic solvent from the first filtrate. The recovered organic solvent can be circulated to step A1 and mixed with the taurine mother liquor, so as to effective reduce an amount of the organic solvent, thereby saving the cost.

In the first solid product separated out from the suspension, the inorganic salts have a pretty low solubility in the ammonia source. However, effective ingredients such as taurine, alkali metal taurate, alkali metal ditaurate, alkali metal tritaurate, alkali metal isethionate and the like can solute in the ammonia source. Thus, in step A3, the inorganic salt impurities, i.e., the second solid product, can be removed by dissolving the first solid product in the ammonia source, so as to recover the second filtrate containing the effective ingredients, such as taurine, alkali metal taurate, alkali metal ditaurate, alkali metal tritaurate, alkali metal isethionate and the like.

Of course, in order to avoid influence of the residual organic solvent in the first solid product, before dissolving the first solid product in the ammonia source, step A3 can further include drying the first solid product to make a mass fraction of the organic solvent in the first solid product less than or equal to 2%. In some embodiments, the mass fraction of the organic solvent in the first solid product can be less than or equal to 0.5%.

In some embodiments, the ammonia source can include a saturated ammonium hydroxide, which has a mass concentration in a range of 25% to 40%.

In order to make the effective ingredients in the first solid product to fully dissolve in the ammonia source and separate from the inorganic salts, a mass of the ammonia source can be 4 times to 15 times of a mass of the dried first solid product. In some embodiments, the mass of the ammonia source can be 4 times to 15 times of a mass of the dried first solid product. In some embodiments, the mass of the ammonia source can be 6 times to 8 times of a mass of the dried first solid product.

Therefore, the method for recovering the taurine mother liquor in the present disclosure is simple to operate, and has a good purification effect. In the method of the present disclosure, materials can be circulated in the reaction to reduce discharging of waste liquor. The method of the present disclosure is environmentally friendly and economical.

Figure 2:
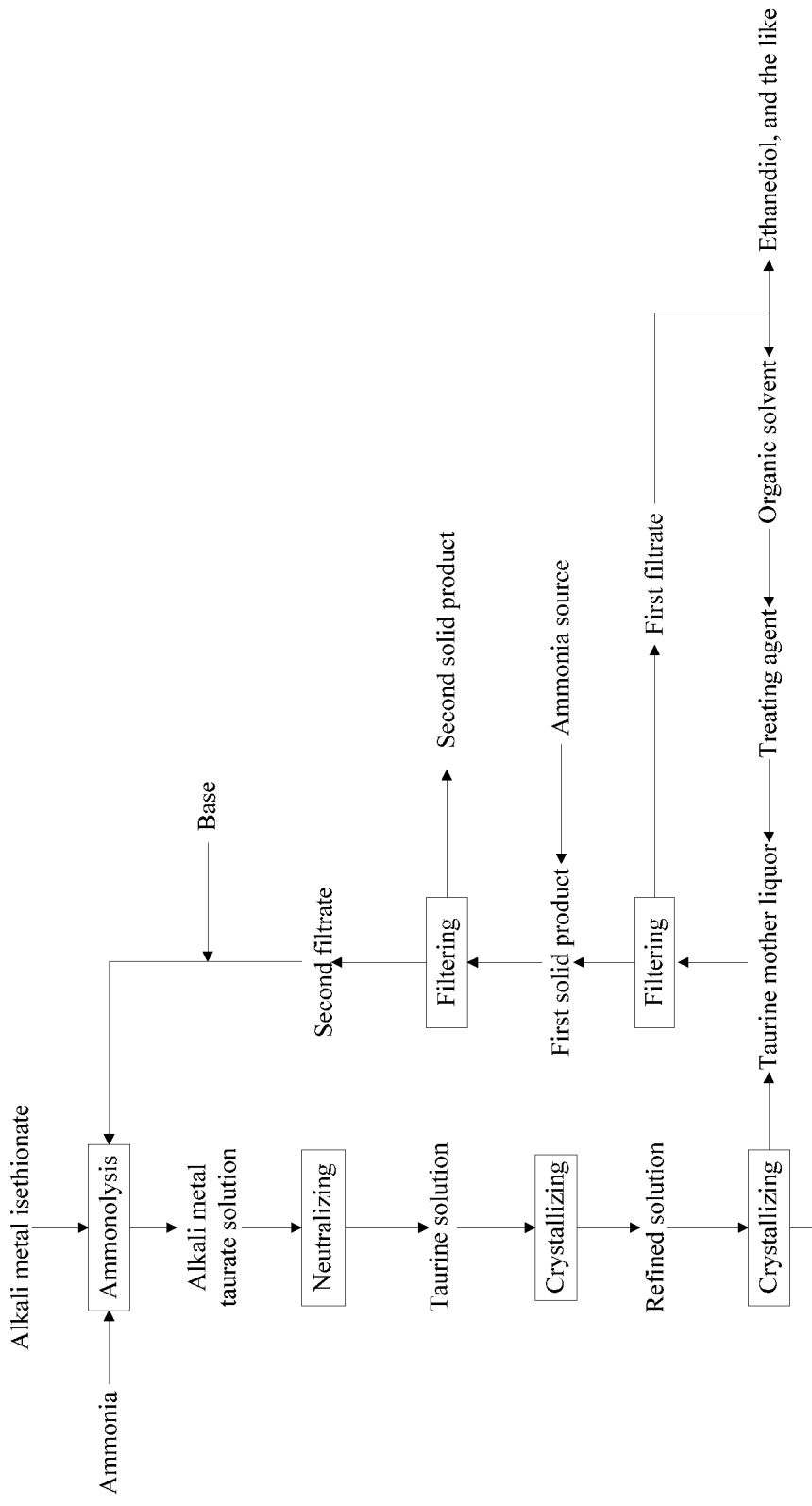
FIG. 2 is a flowchart of a method for preparing taurine in the present disclosure.

FIG. 2 is a flowchart of a method for preparing taurine in the present disclosure, which includes:

B1, providing an alkali metal isethionate, and mixing the alkali metal isethionate with ammonia to carry out an ammonolysis reaction to obtain an alkali metal taurate solution;

B2, subjecting the alkali metal taurate solution to neutral reaction to obtain a taurine solution;

B3, crystalizing the taurine solution to obtain taurine and the taurine mother liquor; and B4, recovering the taurine mother liquor via the method of the present disclosure to obtain the second filtrate.

In step B1, a temperature of the ammonolysis reaction can be in a range of 180° C. to 290° C., and a pressure of the ammonolysis reaction can be in a range of 10 MPa to 20 MPa.

In step B2, strong acids such as sulfate acid, hydrochloric acid and the like can be used to neutralize the alkali metal taurate solution. Optionally, acid gases, such as $CO_2$, $SO_2$ and the like, can be used to neutralize the alkali metal taurate solution. Optionally, acid resins can be used to neutralize the alkali metal taurate solution.

In step B3, water can be used to crystalize the taurine solution. A number of the crystallization process can be over two.

In step B4, the recovered second filtrate can be circulated to step B1 to carry out the ammonolysis reaction. In some embodiments, the method can include mixing the second filtrate obtained with a base to obtain a second mixture, so as to facilitate the ammonolysis reaction. A mass ratio of the base to the second filtrate is in a range of 0.5:100 to 5:100. In some embodiments, the mass ratio of the base to the second filtrate is in a range of 1:100 to 3:100. The base can be at least one selected from NaOH, KOH, $Na_2CO_3$ and $NaHCO_3$.

Therefore, in the method for preparing taurine in the present disclosure, recovery of effective ingredients, such as taurine, alkali metal taurate, alkali metal ditaurate, alkali metal tritaurate, alkali metal isethionate, and the like, in the taurine mother liquor is high, and removal rate of impurities, such as inorganic salt, ethanediol, polyether and the like, is high. Thus, the recovered effective ingredients can be better circulated to the ammonolysis reaction. Therefore, materials can be circulated in the reaction to reduce discharging of waste liquor. The method of the present disclosure is environmentally friendly and economical, and can prevent inorganic salts from accumulating in the circulating process, thereby reducing potential safety hazards.

The method for preparing taurine and the method for recovering a taurine mother liquor will be further illustrated in conjunction with specific embodiments hereinafter.

Embodiment 1

700 g of secondary crude taurine mother liquor (effective ingredients: taurine, sodium taurate, sodium ditaurate, sodium tritaurate and sodium isethionate, having a total mass of 310.03 g) was slowly dropwise added into 6 L of alcohol, stirred to precipitate, and filtrated to obtain a first filtrate and a first solid product. The first filtrate was rectified to recover the alcohol. The first solid product can be dried until a content of the alcohol in the first solid product was less than 0.5%, and 339.62 g of dried first solid was obtained (the effective ingredients was 292.98 g). The yield of the effective ingredients was about 94.5%.

The dried first solid product was added into 2000 g of saturated ammonium hydroxide having a mass concentration of 30%, stirred to dissolve and filtrated to obtain a second solid product (i.e., inorganic impurities such as sodium sulfate and the like) and 2281 g of a second filtrate. The second filtrate was tested, and the ingredients of the second filtrate were shown in Table 1.

TABLE 1

| | In the taurine mother liquor/ wt % | In the second filtrate/ wt % |
|---|---|---|
| Mass fraction of ethanediol | 1.40 | 0.013 |
| Mass fraction of sodium sulfate | 5.69 | 0.17 |
| Mass fraction of taurine | 7.16 | 2.19 |
| Mass fraction of sodium taurate | 3.85 | 1.17 |
| Mass fraction of sodium isethionate | 8.10 | 2.47 |
| Mass fraction of sodium ditaurate | 23.08 | 7.05 |
| Mass fraction of sodium tritaurate | 2.10 | 0.64 |

Embodiment 2

700 g of secondary crude taurine mother liquor (effective ingredients: taurine, sodium taurate, sodium ditaurate, sodium tritaurate and sodium isethionate, having a total mass of 310.03 g) was slowly dropwise added into 6 L of alcohol, stirred to precipitate, and filtrated to obtain a first filtrate and a first solid product. The first filtrate was rectified to recover the alcohol. The first solid product can be dried until a content of the alcohol in the first solid product was less than 0.5%, and 339.62 g of dried first solid was obtained (the effective ingredients was 292.98 g). The yield of the effective ingredients was about 94.5%.

The dried first solid product was added into 2000 g of saturated ammonium hydroxide having a mass concentration of 30%, stirred to dissolve and filtrated to obtain a second solid product (i.e., inorganic impurities such as sodium sulfate and the like) and 2281 g of a second filtrate.

17.7 g of $Na_2CO_3$ was added into the second filtrate, and stirred to dissolve. The resultant was added into a mixture of sodium isethionate and ammonium hydroxide for ammonolysis reaction. The temperature of the ammonolysis reaction was 250° C., and a pressure of the ammonolysis reaction was 19 MPa. After the reaction, ammonia was removed by flash evaporation, so as to obtain a sodium taurate solution. Ammonolysis yield of the embodiment and ingredients of the product were shown in Table 2.

Embodiment 3

3.5 L of methanol was slowly dropwise added into 700 g of secondary crude taurine mother liquor (effective ingredients: taurine, sodium taurate, sodium ditaurate, sodium tritaurate and sodium isethionate, having a total mass of 310.03 g), stirred to precipitate, and filtrated to obtain a first filtrate and a first solid product. The first filtrate was rectified to recover the methanol. The first solid product can be dried until a content of the methanol in the first solid product was less than 0.2%, and 334.39 g of dried first solid was obtained (the effective ingredients was 287.71 g). The yield of the effective ingredients was about 92.8%.

The dried first solid product was added into 2000 g of saturated ammonium hydroxide having a mass concentration of 30%, stirred to dissolve and filtrated to obtain a second solid product (i.e., inorganic impurities such as sodium sulfate and the like) and 2277 g of a second filtrate.

20 g of $Na_2CO_3$ and 26 g of NaOH were added into the second filtrate, and stirred to dissolve. The resultant was added into a mixture of sodium isethionate and ammonium hydroxide for ammonolysis reaction. The temperature of the ammonolysis reaction was 280° C., and a pressure of the ammonolysis reaction was 15 MPa. After the reaction, ammonia was removed by flash evaporation, so as to obtain a sodium taurate solution Ammonolysis yield of the embodiment and ingredients of the product were shown in Table 2.

Embodiment 4

700 g of secondary crude taurine mother liquor (effective ingredients: taurine, sodium taurate, sodium ditaurate, sodium tritaurate and sodium isethionate, having a total mass of 310.03 g) was slowly dropwise added into 10 L of acetone, stirred to precipitate, and filtrated to obtain a first filtrate and a first solid product. The acetone was recovered by permeable membranes. The first solid product can be dried until a content of the acetone in the first solid product was less than 0.3%, and 344.52 g of dried first solid was obtained (the effective ingredients was 297.63 g). The yield of the effective ingredients was about 96%.

The dried first solid product was added into 2000 g of saturated ammonium hydroxide having a mass concentration of 30%, stirred to dissolve and filtrated to obtain a second solid product (i.e., inorganic impurities such as sodium sulfate and the like) and 2484 g of a second filtrate.

12 g of $Na_2CO_3$ and 12 g of $NaHCO_3$ were added into the second filtrate, and stirred to dissolve. The resultant was added into a mixture of sodium isethionate and ammonium hydroxide for ammonolysis reaction. The temperature of the ammonolysis reaction was 260° C., and a pressure of the ammonolysis reaction was 14 MPa. After the reaction, ammonia was removed by flash evaporation, so as to obtain a sodium taurate solution Ammonolysis yield of the embodiment and ingredients of the product were shown in Table 2.

Embodiment 5

700 g of secondary crude taurine mother liquor (effective ingredients: taurine, sodium taurate, sodium ditaurate, sodium tritaurate and sodium isethionate, having a total mass of 310.03 g) was slowly dropwise added into 10 L of methanol aqueous solution (containing 30% of water by mass), stirred to precipitate, and filtrated to obtain a first filtrate and a first solid product. The first filtrate was rectified to recover the methanol. The first solid product can be dried until a content of the methanol in the first solid product was less than 0.4%, and 327.33 g of dried first solid was obtained (the effective ingredients was 281.78 g). The yield of the effective ingredients was about 90.89%.

The dried first solid product was added into 2000 g of saturated ammonium hydroxide having a mass concentration of 30%, stirred to dissolve and filtrated to obtain a second solid product (i.e., inorganic impurities such as sodium sulfate and the like) and 2265 g of second filtrate.

25 g of NaOH was added into the second filtrate, and stirred to dissolve. The resultant was added into a mixture of sodium isethionate and ammonium hydroxide for ammonolysis reaction. The temperature of the ammonolysis reaction was 240° C., and a pressure of the ammonolysis reaction was 18 MPa. After the reaction, ammonia was removed by flash evaporation, so as to obtain a sodium taurate solution. Ammonolysis yield of the embodiment and ingredients of the product were shown in Table 2.

Embodiment 6

700 g of secondary crude taurine mother liquor (effective ingredients: taurine, sodium taurate, sodium ditaurate, sodium tritaurate and sodium isethionate, having a total mass of 310.03 g) was slowly dropwise added into 10 L of acetone aqueous solution (containing 10% of water by mass), stirred to precipitate, and filtrated to obtain a first filtrate and a first solid product. The acetone was recovered by permeable membranes. The first solid product can be dried until a content of the acetone in the first solid product was less than 0.5%, and 321.35 g of dried first solid was obtained (the effective ingredients was 275.93 g). The yield of the effective ingredients was about 89%.

The dried first solid product was added into 2000 g of saturated ammonium hydroxide having a mass concentration of 30%, stirred to dissolve and filtrated to obtain a second solid product (i.e., inorganic impurities such as sodium sulfate and the like) and 2255 g of a second filtrate.

40 g of $Na_2CO_3$ was added into the second filtrate, and stirred to dissolve. The resultant was added into a mixture of sodium isethionate and ammonium hydroxide for ammonolysis reaction. The temperature of the ammonolysis reaction was 260° C., and a pressure of the ammonolysis reaction was 15 MPa. After the reaction, ammonia was removed by flash evaporation, so as to obtain a sodium taurate solution. Ammonolysis yield of the embodiment and ingredients of the product were shown in Table 2.

Embodiment 7

700 g of secondary crude taurine mother liquor (effective ingredients: taurine, sodium taurate, sodium ditaurate, sodium tritaurate and sodium isethionate, having a total mass of 310.03 g) was slowly dropwise added into 10 L of ethanol-acetone aqueous solution (containing 10% of water by mass), stirred to precipitate, and filtrated to obtain a first filtrate and a first solid product. The first filtrate was rectified to recover the ethanol and the acetone. The first solid product can be dried until a total content of the ethanol and the acetone in the first solid product was less than 1%, and 324.83 g of dried first solid was obtained (the effective ingredients was 279.34 g). The yield of the effective ingredients was about 90.1%.

The dried first solid product was added into 2000 g of saturated ammonium hydroxide having a mass concentration of 30%, stirred to dissolve and filtrated to obtain a second solid product (i.e., inorganic impurities such as sodium sulfate and the like) and 2258 g of a second filtrate.

35 g of $NaHCO_3$ was added into the second filtrate, and stirred to dissolve. The resultant was added into a mixture of sodium isethionate and ammonium hydroxide for ammonolysis reaction. The temperature of the ammonolysis reaction was 280° C., and a pressure of the ammonolysis reaction was 10 MPa. After the reaction, ammonia was removed by flash evaporation, so as to obtain a sodium taurate solution. Ammonolysis yield of the embodiment and ingredients of the product were shown in Table 2.

Embodiment 8

700 g of secondary crude taurine mother liquor (effective ingredients: taurine, sodium taurate, sodium ditaurate, sodium tritaurate and sodium isethionate, having a total mass of 310.03 g) was slowly dropwise added into 8 L of acetaldehyde, stirred to precipitate, and filtrated to obtain a first filtrate and a first solid product. The first filtrate was rectified to recover the acetaldehyde. The first solid product can be dried until a content of the acetaldehyde in the first solid product was less than 0.2%, and 337.16 g of dried first solid was obtained (the effective ingredients was 288.95 g). The yield of the effective ingredients was about 93.2%.

The dried first solid product was added into 2000 g of saturated ammonium hydroxide having a mass concentration of 30%, stirred to dissolve and filtrated to obtain a second solid product (i.e., inorganic impurities such as sodium sulfate and the like) and 2264 g of second filtrate.

21 g of $Na_2CO_3$ was added into the second filtrate, and stirred to dissolve. The resultant was added into a mixture of sodium isethionate and ammonium hydroxide for ammonolysis reaction. The temperature of the ammonolysis reaction was 280° C., and a pressure of the ammonolysis reaction was 18 MPa. After the reaction, ammonia was removed by flash evaporation, so as to obtain a sodium taurate solution. Ammonolysis yield of the embodiment and ingredients of the product were shown in Table 2.

Embodiment 9

700 g of secondary crude taurine mother liquor (effective ingredients: taurine, sodium taurate, sodium ditaurate, sodium tritaurate and sodium isethionate, having a total mass of 310.03 g) was slowly dropwise added into 7 L of n-propanol aqueous solution (containing 20% of water by mass), stirred to precipitate, and filtrated to obtain a first filtrate and a first solid product. The first filtrate was rectified to recover the n-propanol. The first solid product can be dried until a content of the n-propanol in the first solid product was less than 0.6%, and 332.10 g of dried first solid was obtained (the effective ingredients was 284.61 g). The yield of the effective ingredients was about 91.8%.

The dried first solid product was added into 2000 g of saturated ammonium hydroxide having a mass concentration of 30%, stirred to dissolve and filtrated to obtain a second solid product (i.e., inorganic impurities such as sodium sulfate and the like) and 2259 g of a second filtrate.

22 g of NaOH was added into the second filtrate, and stirred to dissolve. The resultant was added into a mixture of sodium isethionate and ammonium hydroxide for ammonolysis reaction. The temperature of the ammonolysis reaction was 260° C., and a pressure of the ammonolysis reaction was 17 MPa. After the reaction, ammonia was removed by flash evaporation, so as to obtain a sodium taurate solution. Ammonolysis yield of the embodiment and ingredients of the product were shown in Table 2.

Embodiment 10

700 g of secondary crude taurine mother liquor (effective ingredients: taurine, sodium taurate, sodium ditaurate, sodium tritaurate and sodium isethionate, having a total mass of 310.03 g) was slowly dropwise added into 9 L of ethanediol, stirred to precipitate, and filtrated to obtain a first filtrate and a first solid product. The first filtrate was rectified to recover ethanediol. The first solid product can be dried until a content of the ethanediol in the first solid product was less than 0.8%, and 335.71 g of dried first solid was obtained (the effective ingredients was 287.71 g). The yield of the effective ingredients was about 92.8%.

The dried first solid product was added into 2000 g of saturated ammonium hydroxide having a mass concentration of 30%, stirred to dissolve and filtrated to obtain a second solid product (i.e., inorganic impurities such as sodium sulfate and the like) and 2261 g of a second filtrate.

25 g of $Na_2CO_3$ was added into the second filtrate, and stirred to dissolve. The resultant was added into a mixture of sodium isethionate and ammonium hydroxide for ammonolysis reaction. The temperature of the ammonolysis reaction was 270° C., and a pressure of the ammonolysis reaction was 16 MPa. After the reaction, ammonia was removed by flash evaporation, so as to obtain a sodium taurate solution. Ammonolysis yield of the embodiment and ingredients of the product were shown in Table 2.

Comparative Embodiment 1400 g of sodium isethionate was dissolved in 7500 g of ammonium hydroxide to carry out the ammonolysis ration. The temperature of the ammonolysis reaction was 270° C., and a pressure of the ammonolysis reaction was 15 MPa. After the reaction, ammonia was removed by flash evaporation, so as to obtain a sodium taurate solution. The sodium taurate solution contained 1074 g of sodium taurate. The yield of the ammonolysis reaction was 77.24%.

TABLE 2

| | Mass of the second filtrate in circulation | Mass of the sodium isethionate | Mass of sodium taurate obtained in the ammonolysis reaction | Recovery of the ammonolysis reaction (by mass of the sodium isethionate) |
|---|---|---|---|---|
| Embodiment 2 | 2281 g | 1400 g | 1323 g | 95.15% |
| Embodiment 3 | 2277 g | 1400 g | 1307 g | 93.98% |
| Embodiment 4 | 2484 g | 1400 g | 1352 g | 97.23% |
| Embodiment 5 | 2265 g | 1400 g | 1268 g | 91.20% |
| Embodiment 6 | 2255 g | 1400 g | 1253 g | 90.11% |
| Embodiment 7 | 2258 g | 1400 g | 1264 g | 90.90% |
| Embodiment 8 | 2264 g | 1400 g | 1305 g | 93.82% |
| Embodiment 9 | 2259 g | 1400 g | 1324 g | 95.21% |
| Embodiment 10 | 2261 g | 1400 g | 1292 g | 92.93% |
| Comparative Embodiment | 0 | 1400 g | 1074 g | 77.24% |

The technical features of the above-described embodiments may be combined in any combination. For the sake of brevity of description, all possible combinations of the technical features in the above embodiments are not described. However, as long as there is no contradiction between the combinations of these technical features, all should be considered as within the scope of this disclosure.

The above-described embodiments are merely illustrative of several embodiments of the present disclosure, and the description thereof is relatively specific and detailed, but is not to be construed as limiting the scope of the disclosure. It should be noted that a number of variations and modifications may be made by those skilled in the art without departing from the spirit and scope of the disclosure. Therefore, the scope of the disclosure should be determined by the appended claims.

We claim:

1. A method for recovering a taurine mother liquor, comprising:
   A1, providing a taurine mother liquor, and mixing the taurine mother liquor and a treating agent to obtain a solid-containing suspension, wherein the treating agent is a water-soluble organic solvent or a mixture of the water-soluble organic solvent and water;

A2, filtering the suspension to obtain a first solid product and a first filtrate; and A3, dissolving the first solid product with an ammonia source to obtain a first mixture, and then filtering the first mixture to obtain a second solid product and a second filtrate, wherein the taurine mother liquor is a solution containing impurities comprising taurine, sodium taurate, sodium ditaurate, sodium tritaurate, sodium isethionate, organic impurities and inorganic impurities, the organic impurities comprise ethanediol, polyethylene glycol, and polyether, and the inorganic impurities comprise sulfates, in step A3, before dissolving the first solid product in the ammonia source, the method further comprises:

drying the first solid product to make a mass fraction of the organic solvent in the first solid product less than or equal to 2%, the ammonia source in step A3 comprises a saturated ammonium hydroxide, and in step A3, the mass of the ammonia source is 4 times to 15 times of a mass of the dried first solid product.

2. The method of claim 1, wherein a mass ratio of the taurine mother liquor and the water-soluble organic solvent in step A1 is in a range of 1:1 to 1:20.

3. The method of claim 1, wherein the water-soluble organic solvent in step A1 is at least one selected from alcohol, ketone and aldehyde.

4. The method of claim 3, wherein, the alcohol comprises at least one selected from alcohols containing one to six carbon atoms, the ketone comprises at least one selected from acetone, butanone and methyl vinyl ketone, and the aldehyde is at least one selected from aldehydes containing one to five carbon atoms.

5. The method of claim 1, wherein when the treating agent is the mixture of the water-soluble organic solvent and water, and a mass fraction of water in the mixture is less than or equal to 50%.

6. The method of claim 1, wherein, in step A1, the process of mixing the taurine mother liquor with the treating agent comprises:

adding the taurine mother liquor into the treating agent in batches, or adding the treating agent into the taurine mother liquor in batches.

7. The method of claim 1, wherein the first filtrate in step A2 comprises ethanediol and the water-soluble organic solvent, and step A2 further comprises separating and recovering the water-soluble organic solvent.

8. The method of claim 7, further comprising, circulating the recovered organic solvent to step A1, and mixing the recovered water-soluble organic solvent with the taurine mother liquor.

9. A method for preparing taurine, comprising:

B1, providing a sodium isethionate, and mixing the sodium isethionate with ammonia to carry out an ammonolysis reaction to obtain a sodium taurate solution;

B2, subjecting the sodium taurate solution to neutralization to obtain a taurine solution;

B3, crystallizing the taurine in the taurine solution to obtain taurine and a taurine mother liquor; and B4, recovering the taurine mother liquor via the method of claim 1 to obtain the second filtrate.

10. The method of claim 9, further comprising, mixing the second filtrate obtained in step B4 with a base to obtain a second mixture, and circulating the second mixture to step B1 to carry out the ammonolysis reaction.

11. The method of claim 10, wherein a mass ratio of the base to the second filtrate is in a range of 0.5:100 to 5:100, and the base is at least one selected from NaOH, $Na_2CO_3$ and $NaHCO_3$.

* * * * *